United States Patent [19]
Luzio et al.

[11] Patent Number: 5,820,608
[45] Date of Patent: Oct. 13, 1998

[54] METHOD FOR IN VIVO CHEMICALLY TRIGGERED DISINTEGRATION OF MEDICAL DEVICE

[75] Inventors: Gary Andrew Luzio, Newark; Samuel Anthony Thompson, Wilmington, both of Del.

[73] Assignee: Hercules Incorporated, Wilmington, Del.

[21] Appl. No.: 621,868

[22] Filed: Mar. 18, 1996

Related U.S. Application Data

[62] Division of Ser. No. 128,952, Sep. 29, 1993, Pat. No. 5,531,716.

[51] Int. Cl.⁶ .......................... A61M 5/32; A61M 25/00
[52] U.S. Cl. .................... 604/265; 424/426; 424/78.1
[58] Field of Search .......................... 604/890.1, 891.1, 604/19, 265, 266; 424/422, 423, 426, 78.08, 78.1, 78.11; 623/11, 12

[56] References Cited

U.S. PATENT DOCUMENTS

| | | |
|---|---|---|
| 2,485,512 | 10/1949 | Rose . |
| 2,541,804 | 2/1951 | Wormell . |
| 2,712,672 | 7/1955 | Calcagno . |
| 2,847,713 | 8/1958 | Weingand . |
| 2,897,547 | 8/1959 | Weingand . |
| 3,271,496 | 9/1966 | Michaels . |
| 4,286,341 | 9/1981 | Greer et al. . |
| 4,339,295 | 7/1982 | Boretos et al. . |
| 4,439,322 | 3/1984 | Sonoda et al. . |
| 4,582,865 | 4/1986 | Balazs et al. . |
| 4,605,691 | 8/1986 | Balazs et al. . |
| 4,636,524 | 1/1987 | Balazs et al. . |
| 4,716,154 | 12/1987 | Malson et al. . |
| 4,716,224 | 12/1987 | Sakurai et al. . |
| 4,801,475 | 1/1989 | Halpern et al. . |
| 4,814,120 | 3/1989 | Huc et al. . |
| 4,851,521 | 7/1989 | dellaValle et al. . |
| 4,863,907 | 9/1989 | Sakurai et al. . |
| 4,878,907 | 11/1989 | Okada et al. . |
| 4,888,016 | 12/1989 | Langerman . |
| 4,902,295 | 2/1990 | Walthall et al. . |
| 4,941,870 | 7/1990 | Okada et al. . |
| 4,957,744 | 9/1990 | dellaValle et al. . |
| 4,965,353 | 10/1990 | dellaValle et al. . |
| 4,997,443 | 3/1991 | Walthall et al. . |
| 5,057,606 | 10/1991 | Garbe . |
| 5,085,629 | 2/1992 | Goldbert et al. . |
| 5,089,606 | 2/1992 | Cole et al. . |
| 5,128,326 | 7/1992 | Balazs et al. . |
| 5,149,543 | 9/1992 | Cohen et al. . |
| 5,202,431 | 4/1993 | DellaValle et al. . |

FOREIGN PATENT DOCUMENTS

| | | |
|---|---|---|
| 0213908 | 3/1987 | European Pat. Off. . |
| 0271216 | 6/1988 | European Pat. Off. . |
| 0341745 | 11/1989 | European Pat. Off. ........ C08B 15/00 |
| 0380254 | 8/1990 | European Pat. Off. . |
| 0454373 A2 | 10/1991 | European Pat. Off. . |
| 0507604 | 4/1992 | European Pat. Off. ..... A61K 31/725 |
| 62-33855 | 2/1987 | Japan . |
| 4-146218 A | 5/1992 | Japan . |
| 579004 | 11/1943 | United Kingdom . |
| 2151244 | 8/1984 | United Kingdom ............ C08B 37/00 |
| WO90/10020 | 2/1990 | WIPO ........................ C08B 37/08 |
| WO92/13579 | 8/1992 | WIPO ........................ A61L 31/00 |

OTHER PUBLICATIONS

Andrade, Joseph D., "Hydrogels for Medical and Related Applications", Aug. 27–28, 1975, pp. 1–37, (Editor, presented article at that time); Am. Chem. Soc. 1976.

Kocvara et al., "Gel–Fabric Prostheses of the Ureter", *Journal of Biomedical Research*, vol. 1, pp. 325–326 (1967).

Ross, "Living Cure" (Science and the Citizen), *Scientific American*, Jun. 1993, pp. 18–22.

*Primary Examiner*—Wynn Wood Coggins
*Assistant Examiner*—Jennifer R. Sadula
*Attorney, Agent, or Firm*—Martin F. Sloan

[57] ABSTRACT

The present invention provides medical devices comprised of ionically crosslinked polymer, especially, stents, catheter or cannula components, plugs, and constrictors. The medical devices of the present invention are prepared by treatment of ionically crosslinkable polymer compositions with crosslinking ion compositions to provide ionically crosslinked materials.

An important aspect of the present invention is that these medical devices can be disintegrated in-vivo at a desired time through the exposure of the medical device to a chemical trigger which generally is described as an agent that acts to displace the crosslinking ion in the ionically crosslinked material through binding or simple replacement with a non-crosslinking ion.

52 Claims, 3 Drawing Sheets

METHOD FOR IN VIVO CHEMICALLY TRIGGERED DISINTEGRATION OF MEDICAL DEVICE

This application is a division of application Ser. No. 08/128,952, filed Sept. 29,1993 now U.S. Pat. No. 5,531, 716.

FIELD OF THE INVENTION

This invention relates to medical devices which can be caused to be disintegrated in-vivo. More specifically the present invention relates to novel medical device systems designed for triggered disintegration comprising one or more ionically crosslinkable polymers, one or more crosslinking ions, and one or more agents which displace the crosslinking ion.

BACKGROUND OF THE INVENTION

Medical devices are often used to facilitate the flow of material as, for example, in a ureteral stent used for drainage of urine from the kidney to the bladder, or in a vascular graft used to maintain blood flow.

Typically these medical devices have been made from durable, non-biodegradable materials such as metals, polyurethanes, polyacrylates, etc. These non-biodegradable, non-dissolvable medical devices typically must be removed via an invasive procedure after they have served their purpose, or they remain in the body indefinitely. For those devices which remain in-vivo, there are often medical complications such as inflammation and other foreign body responses.

Devices have also more recently been prepared from biodegradable materials such as polyesters, polyanhydrides, and polyorthoesters. In U. S. Pat. No. 5,085,629, the use of a biodegradable polyester terpolymer of lactide, glycolide, and epsilon-caprolactone in a ureteral stent is disclosed. In the '629 patent, biodegradable has been defined to include hydrolytic instability. These polymers undergo hydrolytic chain cleavage in the presence of water to form low molecular weight water soluble species. The polyesters have been reported to undergo hydrolysis throughout the thickness of the device simultaneously (homogeneous hydrolysis) while the polyanhydrides and polyorthoesters have been reported to hydrolyse from the surface (heterogeneous hydrolysis). There are several problems inherent to devices manufactured with these biodegradable materials. There is a significant loss of strength in the device prior to any significant weight loss. These devices may undergo failure into large pieces which may occlude the vessel in which they have been deployed. Biodegradable devices which undergo surface hydrolysis may eventually reach a thin skin configuration that may also lead to vessel occlusion. Semicrystalline biodegradable materials have also been shown to leave insoluble crystalline residuals in the body for very long periods of time.

Polysaccharide—metal salt systems have been used for many years in biomedical applications. In European Patent Application 0 507 604 A2, an ionically crosslinked carboxyl-containing polysaccharide is used in adhesion prevention following surgery. The ionically crosslinked polysaccharide of this invention is left in-vivo. No attempt to dissolve the material is made.

Hydrogels have been widely used in biomedical applications. In U.S. Pat. 4,941,870; 4,286,341 and 4,878,907, a hydrogel is used as a coating on an elastomer base in a vascular prosthesis. This hydrogel remains in-vivo. Kocavara et al in J. Biomed. Mater. Res. vol. 1, pp. 325–336 (1967) have reported using an anastomosis ureteral prosthesis prepared from a poly(hydroxyethyl methacrylate) hydrogel reinforced with polyester fibers. This prosthesis is designed to be left in vivo.

In U.S. Pat. Nos. 4,997,443 and 4,902,295, transplantable artificial pancreatic tissue is prepared from an alginic acid gel precursor, a matrix monomer, and pancreas cells with $Ca^{2+}$ ions and a matrix monomer polymerization catalyst. The calcium-alginic acid is used to provide mechanical integrity to the mixture while the matrix monomer is polymerized after which the calcium-alginic acid is removed with citrate via calcium chelation to leave a porous matrix. This use of the chelate to dissolve the calcium-alginic acid takes place in vitro. The calcium-alginic acid functions as a processing aid not as a structural member in the final artificial tissue device.

Polysaccharide—metal salt hydrogels have also been used to prepare tiny gel capsules containing pancreatic islet cells for the production of insulin. These capsules have been shown by workers at the Veterans Administration Wadsworth Medical Center to effectively control insulin levels in diabetic dogs for two years (Scientific American, June 1992, pp. 18–22). These capsules remain in vivo.

In U.S. Pat. No. 5,057,606 a method and article useful for preparing polysaccharide hydrogels is disclosed. These foamed and non-foamed gelled articles are prepared by mixing together a first component comprising a suspension of a water insoluble di- or tri-valent metal salt in an aqueous solution of a polysaccharide, with a second component comprising an aqueous solution of a water soluble acid optionally to include the water soluble polysaccharide. These gels remain in vivo.

The present invention eliminates the problems associated with the materials discussed above. Hydrolytic instability is not relied upon to facilitate dissolution. The devices of the present invention are disintegrated upon demand through application of an agent, which acts to remove ionic crosslinking species, which may be anionic (mono or poly) or cationic (mono or poly) in nature, via binding or displacement mechanisms. As used herein, the term "disintegration" includes both the breakdown of the device into small particulates as well as into water soluble components. Triggered disintegration eliminates the time uncertainty observed with bioerodible materials from one patient to the next. Methods for triggered disintegration include administering or triggering release of the disintegration agent through the diet, administering the agent directly onto the device in an aqueous solution, encapsulating the agent in the device, parenteral feeding, and enema. Disintegration occurs without significant swelling of the device.

SUMMARY OF THE INVENTION

The present invention provides a medical device comprising at least one member selected from the group consisting of stents, catheter or cannula components, plugs, and constrictors comprised of ionically crosslinked polymer. The medical devices of the present invention are prepared by treatment of ionically crosslinkable polymer compositions with crosslinking ion compositions to provide ionically crosslinked materials. This treatment may involve crosslinking of an aqueous solution of the ionically crosslinkable polymer component in a solution of the crosslinking ion.

In another embodiment of the present invention, is found the novel combination of a medical device comprising ionically crosslinked polymer combined with at least one body fluid selected from the group consisting of urine, bile, feces, blood and intestinal fluids. Another aspect of the present invention is a medical device comprising at least one member selected from the group consisting of stents, catheter or cannula components, plugs, and constrictors, wherein said medical device comprises at least one body fluid selected from the group consisting of urine, bile, feces, blood and intestinal fluids and ionically crosslinked polymer.

Yet another embodiment of the present invention is a medical device comprising at least one member selected from the group consisting of stents, catheter or cannula components, plugs, and constrictors comprised of ionically crosslinked polymer and an agent that acts to displace a crosslinking ion through binding or simple replacement with a non-crosslinking ion. The invention also comprises a method of disintegrating an in vivo medical device comprising treating said in vivo medical device with at least one chemical trigger. These chemical triggers can comprise at least one agent that displaces a crosslinking ion.

The invention further comprises a method for medical treatment of humans and animals comprising introducing thereinto a medical device comprising at least one member selected from the group consisting of stents, catheter or cannula components, plugs and constrictors wherein the medical device comprises ionically crosslinked polymer.

In another embodiment of the present invention, a method for medical treatment of humans and animals comprises introducing thereinto a medical device which comprises ionically crosslinked polymer, followed by disintegration of the medical device with a chemical trigger.

Still another aspect of the present invention is a medical device comprised of ionically crosslinked polymer hydrogel having a water content of less than 90%, for example, less than 85%, and preferably less than 80%, more preferably less than 70% and most preferably, less than 60%.

A method for making a medical device of the present invention comprises crosslinking an ionically crosslinkable polymer with a crosslinking ion. wherein said medical device comprises at least one member selected from the group consisting of stents, catheter or cannula components, plugs and constrictors.

The devices prepared and equilibrated in accordance with the present invention at room temperature have excellent mechanical strength and elasticity, but it has been found that a higher temperature treatment greatly increases the stiffness and resistance to creep of the device. The equilibration of the device above room temperature, typically between 40° C. and 100° C., not only results in improved mechanical performance, but allows a new shape to be set into the device. Densification of the device may occur during this heat treatment step. Unexpectedly, these shaped and densified devices maintain the new shape and density upon return to room temperature. The densification and strengthening of swollen ionically crosslinked compositions via heat treatment also constitutes an aspect of this invention.

One process for manufacturing the articles of the present invention comprises a method of making a tubular shaped article comprising introducing a solution comprising ionically crosslinkable polymer through a die to form a tube, simultaneously pumping a solution comprising crosslinking ion through the formed tube, and extruding the formed tube from said die into a solution comprising crosslinking ion. In this process the crosslinking step may involve shaping of the device as in wet spinning of a tubular device. Alternatively the device may be prepared by molding a latent crosslinking composition such as a one or two part reaction injection molding system. The term "tubular" as used herein, includes not only cylindrical shaped devices having circular cross sections, but also devices having different cross sections as long as such articles have a hollow passageway such as that which distinguishes a tube from a rod.

Another process for the manufacture of the devices of the present invention would be conventional molding techniques such as reaction injection molding wherein the ionically crosslinkable polymer and the crosslinking ion are mixed and introduced into a mold to form an article of the desired configuration.

In accordance with the present invention, the medical device may also be formed in-vivo. Such a method for medical treatment of humans and animals comprises introducing thereinto an ionically crosslinkable polymer and a crosslinking ion followed by crosslinking of said polymer to form a medical device selected from the group consisting of stents, catheter or cannula components, plugs, and constrictors, wherein said medical device comprises ionically crosslinked polymer.

Disintegration of the medical devices of this invention is achieved through exposure of the ionically crosslinked composition to agents which displace the crosslinking ion. Methods for introduction of the agent include: introduction through or triggered release through the diet of the patient, through parenteral feeding, introduction of a solution directly onto the device or through release of encapsulated agent in the device itself, or through an enema. The medical devices of the present invention are thereby removed safely from the body in the form of water soluble components through exposure to agents that displace the crosslinking ion. Disintegration occurs with minimum swelling of the device.

The medical devices of the present invention that comprise tonically crosslinked polymer are especially useful in various systems in the body of animals or humans, including, but not limited to the gastrointestinal, urogenital, cardiovascular, lymphatic, otorhinolaryngological, optical, neurological, integument and muscular systems.

Still another aspect of the present invention is that these medical devices, which comprise ionically crosslinked polymer, are sterilizable at temperatures of at least 121° C.

DETAILED DESCRIPTION OF THE INVENTION

Figure 1:
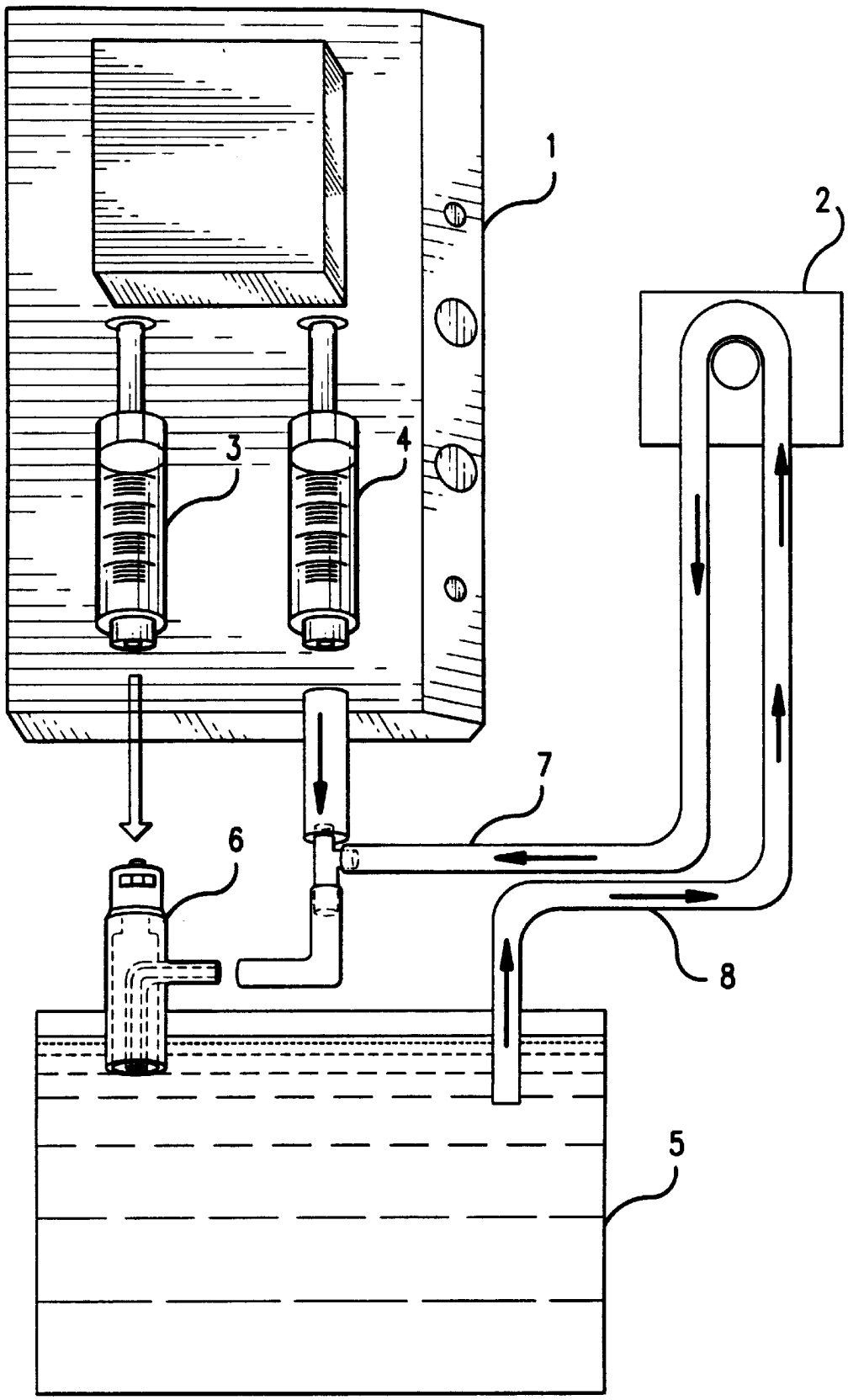
FIG. 1 shows a wet-spinning apparatus used in the practice of the present invention.

The medical devices, of the present invention are prepared by treatment of ionically crosslinkable polymers, with crosslinking ions to provide ionically crosslinked materials.

The ionically crosslinkable polymers may be anionic or cationic in nature and may include but are not limited to carboxylic, sulfate, and amine functionalized polymers such as polyacrylic acid, polymethacrylic acid, polyethylene amine, polysaccharides such as alginic acid, pectinic acid, carboxy methyl cellulose, hyaluronic acid, heparin, chitosan, carboxymethyl chitosan, carboxymethyl starch, carboxymethyl dextran, heparin sulfate, chondroitin sulfate, cationic guar, cationic starch, and their salts. Preferred ionically crosslinkable polymers are alginic acid, pectinic acid, carboxymethyl cellulose, hyaluronic acid, chitosan, and their salts. Most preferred ionically crosslinkable polymers are alginic acid, pectinic acid, and hyaluronic acid and their salts. As previously noted, the ionically crosslinkable polymers employed in the present invention are categorized as ionically crosslinkable anionic polymers and ionically crosslinkable cationic polymers. Among the ionically crosslinkable anionic polymers that may be employed are polyacrylic acid, polymethacrylic acid, alginic acid, pectinic acid, carboxy methyl cellulose, hyaluronic acid, heparin, carboxymethyl starch, carboxymethyl dextran, heparin sulfate, and chondroitin sulfate. Among the ionically crosslinkable cationic polymers that may be employed are chitosan, cationic guar, cationic starch and polyethylene amine.

The crosslinking ions are generally classified as anions or cations. Appropriate crosslinking ions include but are not limited to cations comprising an ion selected from the group consisting of calcium, magnesium, barium, strontium, boron, beryllium, aluminum, iron, copper, cobalt, lead, and silver ions, and anions selected from the group consisting of phosphate, citrate, borate, succinate, maleate, adipate and oxalate ions. More broadly the anions are derived from polybasic organic or inorganic acids. Preferred crosslinking cations are calcium, iron, and aluminum ions. The most preferred crosslinking cations are calcium and iron ions. The most preferred crosslinking anion is phosphate.

Appropriate agents that displace a crosslinking ion include, but are not limited to ethylene diamine tetraacetic acid, ethylene diamine tetraacetate, citrate, organic phosphates, such as cellulose phosphate, inorganic phosphates, as for example, pentasodium tripolyphosphate, mono and di-basic potassium phosphate, sodium pyrophosphate, and phosphoric acid, trisodium carboxymethyloxysuccinate, nitrilotriacetic acid, maleic acid, oxalate, polyacrylic acid, sodium, potassium, calcium and magnesium ions. Preferred agents are citrate, inorganic phosphates, sodium, potassium and magnesium ions. The most preferred agents are inorganic phosphates and magnesium ions.

The devices may optionally include water, other additives for medical treatment such as antiseptics, antibiotics, anticoagulants, or medicines, and additives for mechanical property adjustment.

Linear device or pre-device configurations such as fibers, rods, tubes or ribbons can be manufactured in accordance with the present invention by using a spinning device in which a solution of the ionically crosslinkable polymer is forced through a shaping die into a crosslinking bath containing the crosslinking ions. If the ionically crosslinkable polymer solution is aqueous, the product after crosslinking is typically described as a hydrogel. The hydrogel may be used as made or further given a three dimensional shape through treatment in a crosslinking solution after being forced into the desired shape. After equilibration the hydrogel will retain the new three dimensional shape. The device may be used in its hydrogel form or in a dehydrated form. During dehydration the three dimensional shape is retained.

More complex shaped devices can be made using a one or two part reaction injection molding composition. These molding compositions typically contain the ionically crosslinkable polymer in solution, the crosslinking ion in an insoluble or slowly soluble form and additives to cause dissolution of the crosslinking ion. When the crosslinking ion dissolves and dissociates the tonically crosslinkable polymer solution gels. This gel (or hydrogel if the solvent is water) may be used as made or further developed, crosslinked, and shaped by soaking in a solution of a crosslinking ion. Dissolution of the crosslinking ion to form the gel may be effected by using a two part molding system in which the second component contains an acid or pre-acid such as a cyclic lactone which lowers the pH and solubilizes the previously insoluble crosslinking ion.

The device may then be placed into the body for use. After use the device may be disintegrated in-vivo via exposure to an aqueous solution of an agent which displaces the crosslinking ion.

These medical devices are useful in medical applications where the removal of the standard non-disintegratable medical device involves patient discomfort and/or expense and in applications where a temporary device is therapeutically desirable. Examples of useful applications for these devices include ureteral, urethral, bilial, ileal and pyloric stents. In these applications current state of the art stents must be removed by a second invasive procedure at great expense and patient discomfort. The devices of this invention facilitate removal, leading to reduced patient discomfort and expense. The medical devices of this invention are also useful in cardiovascular, lymphatic, neurological, integumental, skeletal, muscular, optical, otorhinolaryngological, oral, gastrointestinal and urogenital applications where controlled disintegration of the tonically crosslinked portion of the device is efficacious and in surgical procedures where a device is needed temporarily such as a cellular scaffold after which removal by dissolution is preferred. Other medical device applications may include adhesion prevention devices, drainage devices as in ear or sinus tubes, release devices in dental and medical applications, wound care as in the treatment of bed sores, temporary scaffold for bone, osteophilic coatings, neural growth guides, temporary stent for anastomosis, shaped delivery devices, hemostats, surgical sponges, hydrocephalus shunt, dialysis tubing, instrument coatings, patches for delivery systems, ostomy bags, form-fit wound care devices which are gelled on the patient, temporary plug, syringe deliverable temporary fill for aneurism repair, artificial skin, dental socket filler having therapeutic additives, temporary vena cava filter device, capsule for delivery of vena cava filter devices, deep vein thrombosis filter for orthopedic applications, dissolvable enteral feeding tube, enteral plugs, and hiatal hernia stents. Any of these devices may also act to release medicines, nutrients and the like.

The present invention eliminates the problems associated with the prior art materials. Hydrolytic instability is not used to facilitate dissolution. These devices are disintegrated upon demand through application of an agent which displaces the crosslinking ion into the device. Triggered disintegration eliminates the time uncertainty observed with bioerodible materials from one patient to the next. Methods for triggered disintegration include administering or triggering release of the agent through the diet, administering the agent directly onto the device in an aqueous solution, encapsulating the agent in the device, parenteral feeding, and enema. Disintegration occurs without significant swelling of the device.

In FIG. 1 is shown a wet spinning apparatus used to make the medical devices of the present invention. A syringe pump 1 is shown for pumping the contents of syringe 3 and syringe 4. Syringe 3 is filled with the ionically crosslinkable polymer and syringe 4 is filled with the crosslinker, usually a crosslinking ion solution. Syringe 3 is connected to wet spinning die 6 into which is a side tube 7 connected to syringe 4. A crosslinking bath 5 contains the crosslinking ion solution which is recirculated through tube 8 by peristaltic pump 2.

Figure 2:
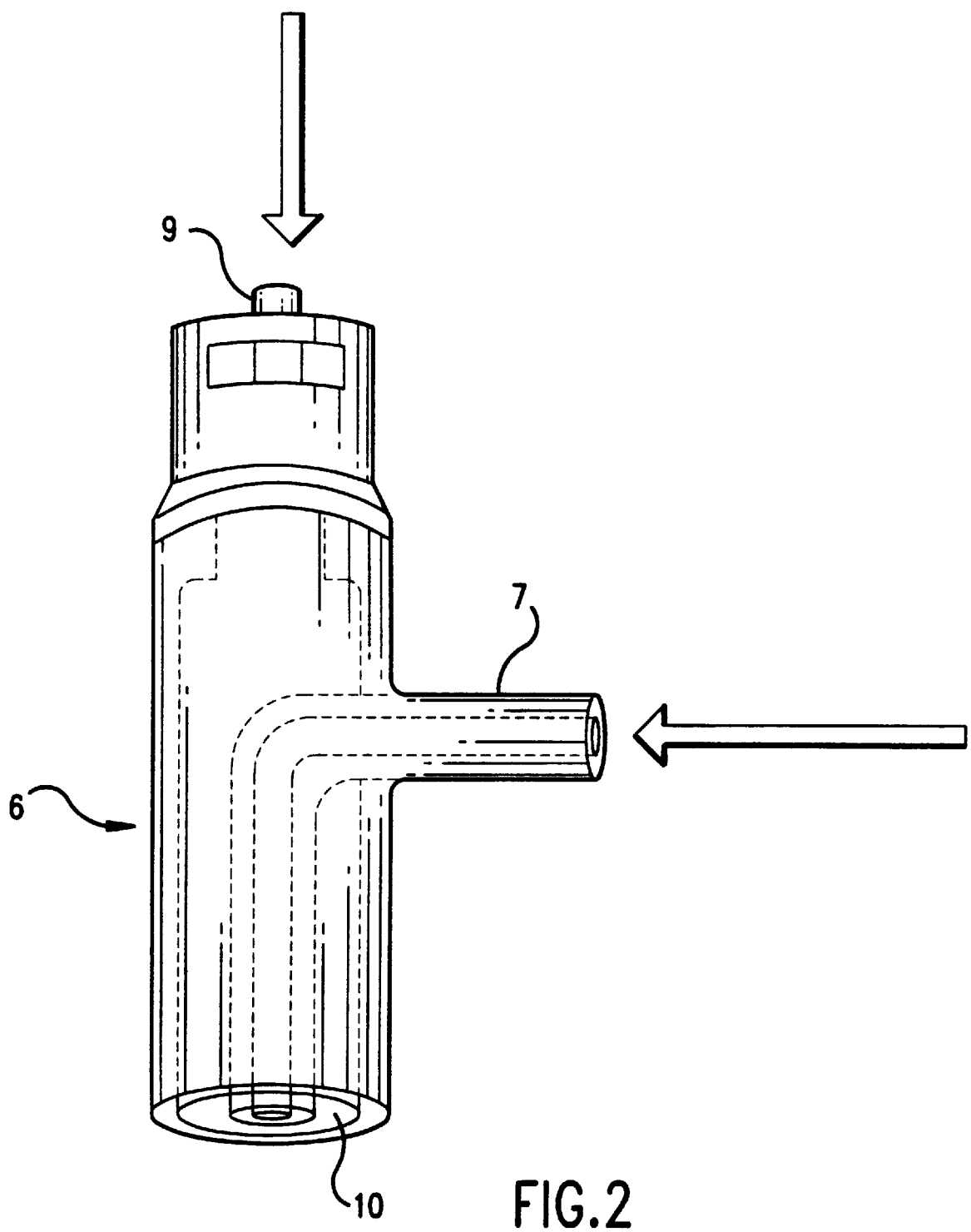
FIG. 2 shows the wet-spinning die that is a part of the apparatus shown in FIG. 1.

In FIG. 2 is shown wet spinning die 6 having an end 9 into which enters the ionically polymerizable polymer and an end 10 out of which comes an article comprising the reaction product of the polymer and crosslinking ion. The crosslinking ion enters through side tube 7 so that as a tube is formed in the wet spinning die, the polymer is contacted with the crosslinking ion on the inside and outer surfaces of the tube.

Figure 3:
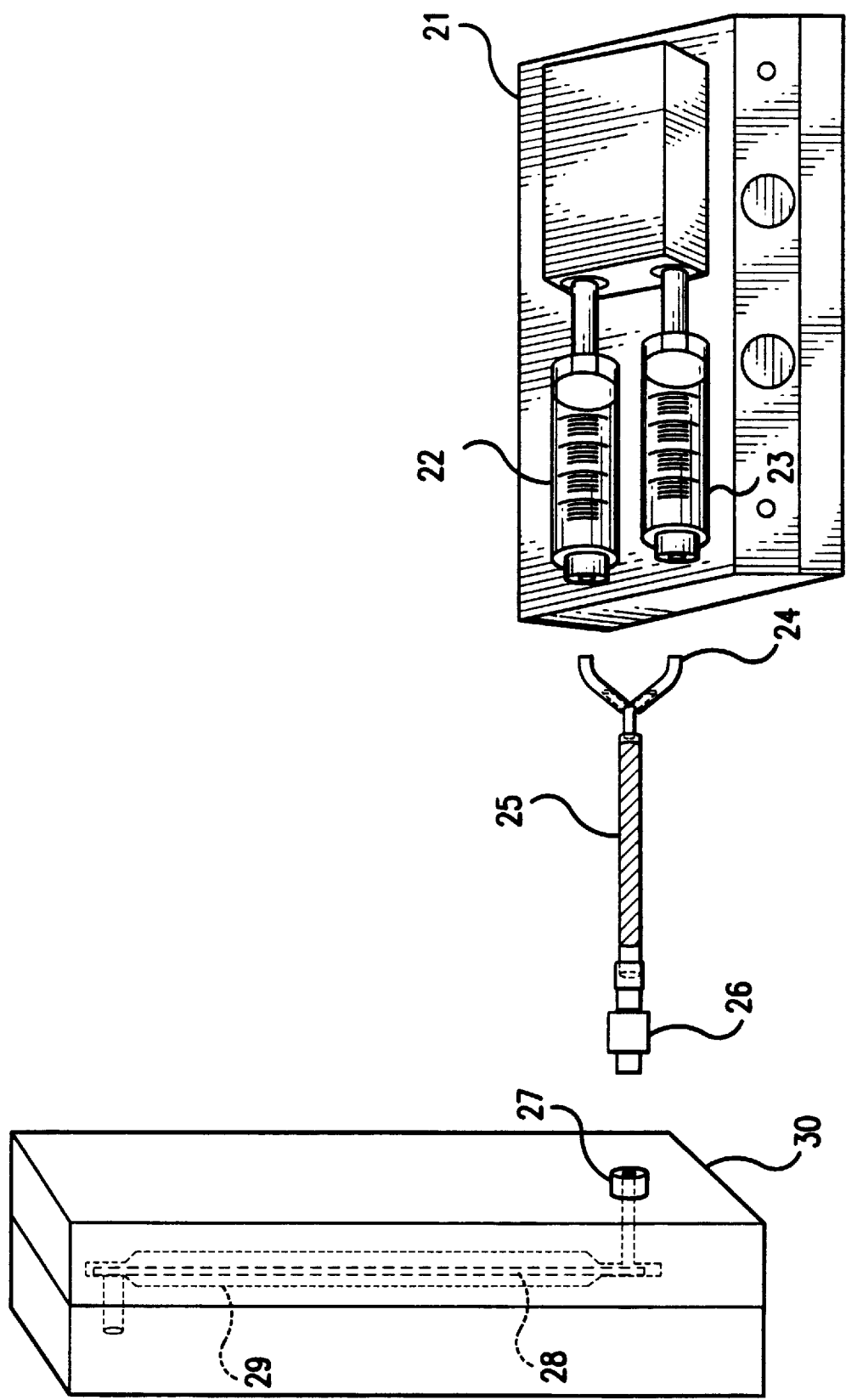
FIG. 3 shows a reaction injection molding set up for manufacture of medical devices of the present invention.

In FIG. 3 is shown a reaction injection molding apparatus used to make medical devices of the present invention having a syringe pump 21 connected to syringe 22 which contains an ionically crosslinkable polymer and an insoluble salt comprising a crosslinking ion and to syringe 23 which contains an ionically crosslinkable polymer and a pH adjuster. The contents of syringes 22 and 23 are injected into y-tube 24 and pass into static mixer 25. Both y-tube 24 and static mixer 25 are silicone tubing. The contents of the static mixer 25 then travel from static mixer end 26 into port 27 of mold 30 having a tubular shaped cavity 29 and a rod 28 positioned so that a tubular shaped device is molded and gels. The gelled tubular shaped device may then be placed in a solution comprising crosslinking ion until a sufficiently crosslinked polymer is made.

The invention is further illustrated by the following examples.

EXAMPLE 1

To 95.10 grams of distilled water was added 5.005 grams of sodium alginic acid (Sigma, medium molecular weight, macrocystis pyrifera) which were mixed until uniform (approximately 1 hour), heated to 90° C. for 45 minutes, cooled to room temperature and then centrifuged to remove trapped air. The sodium alginic acid solution was then used to fill a 30 cc syringe which was attached to the wet spinning die illustrated in FIG. 1. The syringe and die were hooked up as shown in FIG. 1 to a syringe pump, crosslinking solution syringe containing 10% by weight $CaCl_2$ dihydrate in water, and a peristaltic pump feed containing 10% by weight $CaCl_2$ dihydrate in water. The syringe pump was used to wet spin a tube of sodium-alginic acid into a crosslinking bath containing 10% by weight $CaCl_2$ dihydrate in water. After the tube had been spun the peristaltic pump was turned on to maintain the flow of coagulant solution through the tube. After 30 minutes the tube was removed from the crosslinking bath and placed in a 4% by weight $CaCl_2$ dihydrate solution in water. The tube was left in this solution for 24 hours.

EXAMPLE 2

Sections of tube prepared as in Example 1 were immersed in the following aqueous solutions: a) 0.5% monobasic potassium phosphate and 0.5% dibasic potassium phosphate, and b) 1% sodium tripolyphosphate, respectively, and left to stand overnight. The tubes in vials a and b had broken up and disintegrated overnight.

EXAMPLE 3

Tubing prepared as in Example 1 was placed over a copper wire which was then bent at both ends to form pigtails. The tubing and wire were then placed into a 4% by weight $CaCl_2$ dihydrate solution in water which was heated to 90° C. for 12 hours. After cooling the solution to room temperature the tubing and wire were removed from the solution, the wire restraightened and the tubing removed from the wire. The tubing had retained the shape of the wire, now having pigtails on each end and exhibited a decrease in wall thickness.

EXAMPLE 4

A short section of tube cut from tubing which had been heat shaped as in Example 3 was then immersed in a 0.50% by weight sodium citrate solution in water. The tube disintegrated fully in less than 6 hours.

EXAMPLE 5

Approximately 15 grams of a 5% by weight sodium alginic acid solution in water (prepared as in Example 1) was loaded into a 30 cc syringe. The syringe and die were hooked up as shown in FIG. 1 to a syringe pump, crosslinking solution syringe containing 10% by weight $Al_2(SO_4)_3.18H_2O$ in water, and a peristaltic pump feed containing 10% by weight $Al_2(SO_4)_3.18H_2O$ in water. The syringe pump was used to wet spin a tube of sodium alginic acid into a crosslinking bath containing 10% by weight $Al_2(SO_4)_3.18H_2O$ in water. After the tube had been spun the peristaltic pump was turned on to maintain the flow of coagulant solution through the tube. After 20 minutes the tube was removed from the crosslinking bath and placed in a 4% by weight $Al_2(SO_4)_3.18H_2O$ solution in water. The tube was left in this solution for 24 hours. The tube was then heated to 90° C. in the 4% $Al_2(SO_4)_3.18H_2O$ solution in water for 16 hours. A ¼" length of heat treated tube was then shown to dissolve and fall apart in a 0.50% by weight sodium tripolyphosphate in water solution overnight.

EXAMPLE 6

Approximately 2 cc of a 5% by weight sodium alginic acid solution in water prepared as in Example 1 was loaded into a 10 cc syringe from which it was spun into a 4% by weight solution of $FeCl_3$ in water. The solution coagulated immediately to form a continuous fiber. After sitting overnight in the $FeCl_3$ solution, the fiber was heated in the 4% by weight solution of $FeCl_3$ in water for 16 hours at 90 C., then a piece of the fiber was immersed in a 0.50% sodium tripolyphosphate solution in water. The fiber disintegrated overnight.

EXAMPLE 7

A 5% by weight sodium alginic acid solution in water prepared as in Example 1 was spun from a 10 cc syringe into a 4% by weight $SrCl_2.6H_2O$ solution in water. The alginic acid solution gelled immediately to form a fiber. The fiber was left in the crosslinking solution overnight. The following day the fiber was heated for 16 hours at 90° C. in the same crosslinking solution. Short sections of the heat treated fiber were immersed in a 0.5% by weight sodium tripolyphosphate in water solution and a 0.5% by weight sodium citrate in water solution. The fiber in the sodium tripolyphosphate solution disintegrated within 3 hours. The fiber in the sodium citrate solution disintegrated overnight.

EXAMPLE 8

0.010 grams of sodium hyaluronate (Chisso Corp, lot# 700910, MW $1.35 \times 10^6$) were added to 0.99 grams of a 5% by weight sodium alginic acid solution which had been prepared as in example 1. The solution was mixed with a spatula until the hyaluronate had dissolved and the solution was uniform. The solution was then transferred to a 2.5 cc glass syringe. An 18 gauge, 1.5 " long needle was attached to the glass syringe and the sample was spun into a 10% by weight $CaCl_2.2H_2O$ solution in water. The sample gelled quickly to form a fiber. The fiber was left in the crosslinking solution for 1 hour. The fiber was then transferred to a 4% aqueous solution of $CaCl_2.2H_2O$ and left overnight. The fiber was then heated in the 4% aqueous solution of $CaCl_2.2H_2O$ for 16 hours. The fiber was then shown to disintegrate and dissolve in a 0.5% aqueous solution of sodium tripolyphosphate overnight.

EXAMPLE 9

1.25 grams of pectinic acid (GENU® pectinic acid Hercules Incorporated, LM 1912 CSZ) were added to 47.5 grams of distilled water while mixing. Mixing was continued for 15 minutes after which 1.25 grams of sodium alginic acid (Sigma, medium molecular weight) were added. The mixture was mixed for another 30 minutes then centrifuged to remove trapped air. Approximately 2 cc of the solution were loaded into a 2.5 cc syringe. The solution was spun directly from the syringe into a 10% $CaCl_2.2H_2O$ solution in water. The material gelled immediately in the form of a fiber. The fiber was left in the crosslinking solution for 20 minutes then the $CaCl_2.2H_2O$ was diluted down to 4% by the addition of distilled water. The sample was stored in this 4% solution overnight. A small piece of the fiber was shown to dissolve overnight in a 0.5% sodium tripolyphosphate solution in water.

EXAMPLE 10

A 2.9% by weight sodium hyaluronate solution in water was prepared by adding 0.10 grams of sodium hyaluronate (Chisso Corporation) to 3.40 grams of distilled water. 0.73 grams of a 3% aqueous solution of $FeCl_3$ were decanted on top of the sodium hyaluronate solution. The hyaluronate solution began to gel immediately. After 3 hours a small piece of the gel was removed and immersed in a 0.5% aqueous solution of sodium tripolyphosphate. The gel disintegrated overnight.

EXAMPLE 11

0.82 grams of heparin (Fluka) and 0.83 grams of distilled water were weighed into a 5 ml vial, stirred until the heparin dissolved then centrifuged to remove trapped air. An equal volume (approximately 1.6 cc) of a 3% by weight $FeCl_3$ solution in water was then decanted into the 5 ml vial on top of the heparin solution. After sitting overnight at room temperature the heparin solution had gelled. This gel was shown to dissolve fully in a 0.5% sodium tripolyphosphate solution in water within a few hours.

EXAMPLE 12

4.00 grams of Mannugel DMB (Kelco International Limited) were added to 76.00 grams of distilled water while stirring. The sample was stirred for 1 hour at room temperature after which it was heated for 1 hour at 90° C. The sample was then centrifuged to remove trapped air. Approximately 30 cc of the Mannugel solution was transferred to a 30 cc syringe. The syringe was attached to a tube die as in FIG. 1 to a syringe pump, crosslinking solution syringe containing 10% by weight $CaCl_2$ dihydrate in water, and a peristaltic pump feed containing 10% by weight $CaCl_2$ dihydrate in water. The syringe pump was used to wet spin a tube of sodium-alginic acid into a crosslinking bath containing 10% by weight $CaCl_2$ dihydrate in water. After the tube had been spun the peristaltic pump was turned on to maintain the flow of crosslinking solution through the tube. After 20–30 minutes the tube was removed from the crosslinking bath and placed in a 4% by weight $CaCl_2$ dihydrate solution in water. The tube was left in this solution overnight. A piece of the tubing was then heat treated at 90° C. for 16 hours in the 4% by weight $CaCl_2$ dihydrate solution in water. A piece of the heat treated tube was then immersed in a 0.5% by weight sodium tripolyphosphate solution in water. After sitting overnight the tube had fallen apart and disintegrated.

EXAMPLE 13

5.0 grams of pectinic acid (GENU® pectinic acid Hercules Inc., LM 1912 CSZ) were added to 45.0 grams of distilled water while mixing. Another 16.62 grams of distilled water were added and mixed until uniform. The solution was centrifuged to remove trapped air. Approximately 2 cc of the solution were loaded into a 2.5 cc syringe. The solution was spun through a 1.5" long 18 gauge needle into a 10% $CaCl_2.2H_2O$ in water solution. The fiber gelled immediately. The fiber was left in the crosslinking bath for 45 minutes after which it was transferred to a 4% $CaCl_2.2H_2O$ in water solution and left overnight. The fiber in the 4% $CaCl_2.2H_2O$ water solution was then heated to 90° C. for 16 hours. A piece of the fiber was then shown to fully dissolve in a 0.5% sodium tripolyphosphate solution in water.

EXAMPLE 14

2.40 grams of $CaHPO_4$ were dispersed in 76.63 grams of distilled water. 4.00 grams of sodium alginic acid (Sigma, medium molecular weight) were then added to this suspension while mixing. After mixing until uniform the solution/suspension was heated to 90° C. for 20 minutes, mixed in a American Brand Ultrasonic Cleaner Bath for thirty minutes, left overnight at room temperature, then centrifuged to remove trapped air. A second solution was prepared by mixing 0.30 grams of D-gluconic acid lactone (Sigma) into 9.70 grams of a 5% solution of sodium alginic acid in water. Parts 1 and 2 were then loaded into separate 10 cc syringes, fitted as in FIG. 3. The syringe pump was used to force the two solutions through the static mixer into a mold designed to produce a 10" long tube having 0.12" outer diameter and 0.04" inner diameter. After 1.5 hours the mold was opened and the gelled tube removed. The tube was placed into a 4% by weight $CaCl_2.H_2O$ solution in water. After sitting overnight a piece of copper wire was inserted into the tube, shaped such that both ends formed pigtails, then heat treated at 90° C. for 16 hours. The heat shaped tube was then removed from the copper wire. The tube retained the pigtail shape at both ends. A piece of the tube was immersed into a 0.50% solution of sodium tripolyphosphate in water. The tube fell apart and disintegrated overnight.

EXAMPLE 15

About 0.5 ml of a 25% by weight solution of sodium polyacrylic acid (Polysciences, MW of 140,000) were added to about 5 ml of a 4% by weight calcium chloride dihydrate solution in water. The polyacrylic acid formed a gel overnight. A small piece of this gel was shown to dissolve overnight in 10 cc of 0.5% sodium tripolyphosphate.

It is claimed:

1. A method comprising:

a) introducing into humans or animals a medical device comprising ionically crosslinked polymer, followed by b) complete disintegration of with a chemical trigger.

2. The method of claim 1 wherein said chemical trigger comprises at least one agent that displaces a crosslinking ion.

3. The method of claim 2 wherein said agent that displaces a crosslinking ion comprises one or more members selected from the group consisting of ethylene diamine tetra acetic acid, ethylene diamine tetraacetate, citrate, organic phosphates, inorganic phosphates, trisodium carboxymethyloxysuccinate, nitrilotriacetic acid, maleic acid, oxalate, polyacrylic acid, sodium, potassium, calcium and magnesium.

4. The method of claim 3 wherein said organic phosphate is cellulose phosphate.

5. The method of claim 3 wherein said inorganic phosphate is selected from the group consisting of pentasodium tripolyphosphate, mono and di-basic potassium phosphate, sodium pyrophosphate and phosphoric acid.

6. The method of claim 2 wherein said agent that displaces a crosslinking ion comprises one or more members selected from the group consisting of citrates, inorganic phosphates, sodium, potassium and magnesium.

7. The method of claim 2 wherein said agent that displaces a crosslinking ion is selected from the group consisting of inorganic phosphates and magnesium.

8. The method of claim 2 wherein said ionically crosslinked polymer comprises at least one polymer made from at least one ionically crosslinkable polymer selected from the group consisting of carboxylic, sulfate and amine functionalized polymers.

9. The method of claim 1 wherein said ionically crosslinked polymer comprises at least one polymer made from at least one polysaccharide.

10. The method of claim 1 wherein said ionically crosslinked polymer comprises at least one polymer made from at least one ionically crosslinkable anionic polymer.

11. The method of claim 10 wherein said ionically crosslinked anionic polymer comprises at least one polymer made from at least one ionically crosslinkable polymer selected from the group consisting of polyacrylic acid, polymethacrylic acid, alginic acid, pectinic acid, carboxy methyl cellulose, hyaluronic acid, heparin, carboxymethyl starch, carboxymethyl dextran, heparin sulfate, and chondroitin sulfate, and salts thereof.

12. The method of claim 10 wherein said ionically crosslinked anionic polymer comprises at least one polymer made from at least one ionically crosslinkable polymer selected from the group consisting of alginic acid, pectinic acid, carboxymethyl cellulose, hyaluronic acid, and salts thereof.

13. The method of claim 12 wherein said ionically crosslinked anionic polymer comprises at least one polymer made from the group consisting of alginic acid and salts thereof.

14. The method of claim 13 wherein said ionically crosslinked polymer is crosslinked by a crosslinking ion which comprises barium.

15. The method of claim 13 wherein said ionically crosslinked polymer is crosslinked by a crosslinking ion which comprises strontium.

16. The method of claim 13 wherein said ionically crosslinked polymer is crosslinked by a crosslinking ion which comprises copper.

17. The method of claim 13 wherein said ionically crosslinked polymer is crosslinked by a crosslinking ion which comprises lead.

18. The method of claim 1 wherein said ionically crosslinked polymer comprises at least one polymer made from at least one ionically crosslinkable cationic polymer.

19. The method of claim 18 wherein said ionically crosslinked cationic polymer comprises at least one polymer made from at least one ionically crosslinkable polymer selected from the group consisting of chitosan, cationic guar, cationic starch and polyethylene amine.

20. The method of claim 1 wherein said ionically crosslinked polymer is crosslinked by a crosslinking ion which comprises one or more cations.

21. The method of claim 20 wherein said one or more cations are selected from the group consisting of calcium, magnesium, barium, strontium, boron, beryllium, aluminum, iron, copper, cobalt, lead, and silver ions.

22. The method of claim 20 wherein said one or more cations are selected from the group consisting of calcium, iron, and aluminum ions.

23. The method of claim 20 wherein said one or more cations is calcium ion.

24. The method of claim 1 wherein said ionically crosslinked polymer is crosslinked by a crosslinking ion which comprises one or more anions.

25. The method of claim 24 wherein said one or more anions are selected from the group consisting of phosphate, citrate, borate, succinate, maleate, adipate and oxalate ions.

26. The method of claim 24 wherein said one or more anions is phosphate ion.

27. A method for dissolving a medical device present in a human or animal body comprising treating said medical device in vivo with at least one chemical trigger to cause complete disintegration of the medical device.

28. The method of claim 27 wherein said in vivo medical device comprises ionically crosslinked polymer and wherein said chemical trigger comprises at least one agent that displaces a crosslinking ion.

29. The method of claim 28 wherein said agent that displaces a crosslinking ion comprises one or more members selected from the group consisting of ethylene diamine tetra acetic acid, ethylene diamine tetraacetate, citrate, organic phosphates, inorganic phosphates, trisodium carboxymethyloxysuccinate, nitrilotriacetic acid, maleic acid, oxalate, polyacrylic acid, sodium, potassium, calcium and magnesium.

30. The method of claim 28 wherein said organic phosphate is cellulose phosphate.

31. The method of claim 28 wherein said inorganic phosphate is selected from the group consisting of pentasodium tripolyphosphate, mono and di-basic potassium phosphate, sodium pyrophosphate and phosphoric acid.

32. The method of claim 28 wherein said agent that displaces a crosslinking ion comprises one or more members selected from the group consisting of citrates, inorganic phosphates, sodium, potassium and magnesium.

33. The method of claim 28 wherein said agent that displaces a crosslinking ion is selected from the group consisting of inorganic phosphates and magnesium.

34. The method of claim 28 wherein said ionically crosslinked polymer comprises at least one polymer made from at least one ionically crosslinkable polymer selected from the group consisting of carboxylic, sulfate and amine functionalized polymers.

35. The method of claim 28 wherein said ionically crosslinked polymer comprises at least one polymer made from at least one polysaccharide.

36. The method of claim 28 wherein said ionically crosslinked polymer comprises at least one polymer made from at least one ionically crosslinkable anionic polymer.

37. The method of claim 36 wherein said ionically crosslinked anionic polymer comprises at least one polymer made from at least one ionically crosslinkable polymer selected from the group consisting of polyacrylic acid, polymethacrylic acid, alginic acid, pectinic acid, carboxy methyl cellulose, hyaluronic acid, heparin, carboxymethyl starch, carboxymethyl dextran, heparin sulfate, and chondroitin sulfate, and salts thereof.

38. The method of claim 36 wherein said ionically crosslinked anionic polymer comprises at least one polymer made from at least one ionically crosslinkable polymer selected from the group consisting of alginic acid, pectinic acid, carboxymethyl cellulose, hyaluronic acid, and salts thereof.

39. The method of claim 38 wherein said ionically crosslinked anionic polymer comprises at least one polymer made from the group consisting of alginic acid and salts thereof.

40. The method of claim 39 wherein said ionically crosslinked polymer is crosslinked by a crosslinking ion which comprises barium.

41. The method of claim 39 wherein said ionically crosslinked polymer is crosslinked by a crosslinking ion which comprises strontium.

42. The method of claim 39 wherein said ionically crosslinked polymer is crosslinked by a crosslinking ion which comprises copper.

43. The method of claim 39 wherein said ionically crosslinked polymer is crosslinked by a crosslinking ion which comprises lead.

44. The method of claim 28 wherein said ionically crosslinked polymer comprises at least one polymer made from at least one ionically crosslinkable cationic polymer.

45. The method of claim 44 wherein said ionically crosslinked cationic polymer comprises at least one polymer made from at least one ionically crosslinkable polymer selected from the group consisting of chitosan, cationic guar, cationic starch and polyethylene amine.

46. The method of claim 28 wherein said ionically crosslinked polymer is crosslinked by a crosslinking ion which comprises one or more cations.

47. The method of claim 46 wherein said one or more cations are selected from the group consisting of calcium, magnesium, barium, strontium, boron, beryllium, aluminum, iron, copper, cobalt, lead, and silver ions.

48. The method of claim 46 wherein said one or more cations are selected from the group consisting of calcium, iron, and aluminum ions.

49. The method of claim 46 wherein said one or more cations is calcium ion.

50. The method of claim 28 wherein said ionically crosslinked polymer is crosslinked by a crosslinking ion which comprises one or more anions.

51. The method of claim 50 wherein one or more anions are selected from the group consisting of phosphate, citrate, borate, succinate, maleate, adipate and oxalate ions.

52. The method of claim 50 wherein said one or more anions is phosphate ion.

* * * * *

UNITED STATES PATENT AND TRADEMARK OFFICE
CERTIFICATE OF CORRECTION

PATENT NO. : 5,820,608

DATED : October 13, 1998

INVENTOR(S) : Gary A. Luzio and Samuel A. Thompson

It is certified that error appears in the above-identified patent and that said Letters Patent are hereby corrected as shown below:

Claim 1, line 1, column 11
    After "of" insert -- said medical devices--.
Claim 30, line 42, column 12.
    Delete "28" and replace with - -29- - .
Claim 31, line 44, column 12.
    Delete "28" and replace with - -29- - .

Signed and Sealed this

Twenty-third Day of March, 1999

Attest:

Q. TODD DICKINSON

Attesting Officer      Acting Commissioner of Patents and Trademarks